Dec. 9, 1975 C. OLSON Plant Pat. 3,814
STRAWBERRY PLANT
Filed Jan. 6, 1975
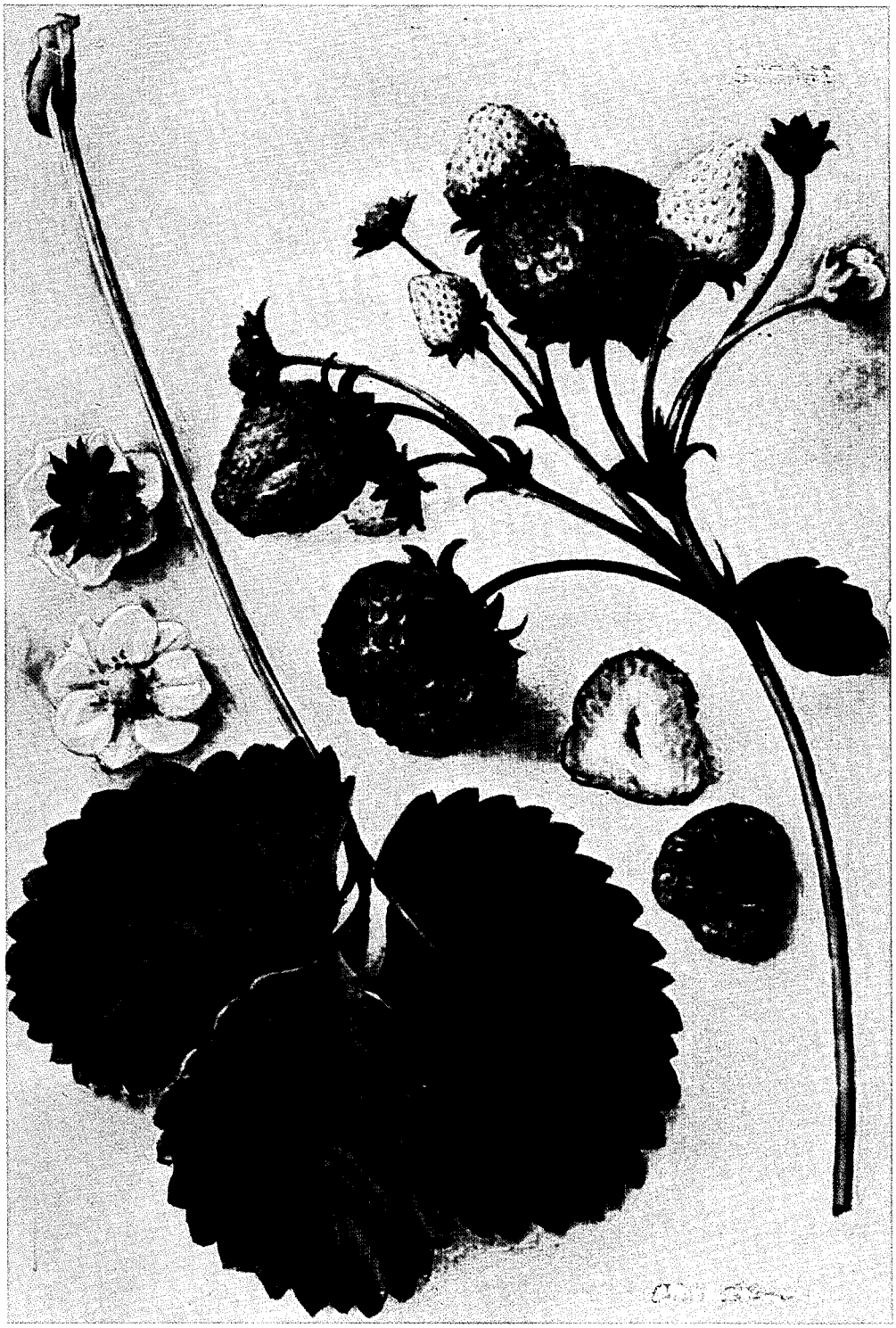

United States Patent

Plant Pat. 3,814

Patented Dec. 9, 1975

3,814

STRAWBERRY PLANT

Christian Olson, Rte. 1, Box 61, Aurora Township, Waushara County, Berlin, Wis. 54923

Filed Jan. 6, 1975, Ser. No. 538,961

Int. Cl. A01h 5/03

U.S. Cl. Plt.—49 1 Claim

This invention relates to a new and distinct variety of strawberry plant designated Ourown which is the result of a cross of the everbearing variety known as the Gem and a June bearing variety known as the Temple.

The seedlings resulting from the aforementioned cross were grown and asexually multiplied on my farm in the township of Aurora, Waushara County, Wis. After growing many of these seedlings I noticed a great variation among them. The best one was then selected, resulting in this new variety. Many plants were then produced asexually from this most outstanding selection. These tests indicated the many merits of this plant.

Plant parts of the new variety, typical in actual size, shape and color are illustrated in the accompanying reproduction of a drawing I have made which is typical of the several parts of the plant in June.

The plant of the present invention was developed for the purpose of obtaining a new variety of everbearing strawberry that would yield a larger fruit with an improved flavor, and would also maintain its vigor, have good growth and possess hardiness to withstand severe winters. One of the parents of this new variety, the Gem, was selected because it was an everbearing variety that was vigorous and hardy, and also produced larger fruit than other everbearing varieties. The Temple was chosen for the other parent because of its flavor, vigor of plant growth and resistance to a strain of red stele.

This novel variety has the desirable qualities of both parent plants, the Gem and Temple. It is an everbearing, growing medium to large in size. The leaves are dark green and glossy. The fruit is not as dark a red as the Temple, but is darker than the Gem, resulting in a plant that yields a medium red fruit. The flavor of the fruit is a decided improvement, compared to the Gem. The flavor is much sweeter. It also maintains its vigor and hardiness through the severely cold wisconsin winters. These characteristics make this variety distinct.

Plants set out in April will produce in the following months of July and August, continuing into September and October, to the time of frost. If plants are again set out the following year in April, a June crop may be picked from last year's planting followed by the harvesting of fruit beginning in July and continuing into October. Adequate irrigation and good fertile soil are necessary to obtain these results. This variety will grow on various soils, from sand to clay types.

The blossoms are easily seen during June and the summer months, later in the fall the blossoms are covered by the leaves, giving them protection from early frost injury.

This new variety produces larger berries than the progressive, Gem, Wayzata, Ogallala and Ozark Beauty. The plant has only a very small amount of leaf spot.

PLANTS

The plants are medium to large in size, vigorous and hardy. A large rugged root system is also characteristic of this plant.

LEAVES

The leaves are medium to large in size. Petioles of these leaves vary in length from 16 cm. to 29½ cm. The petiolules are from 5 mm. to 7 mm. in length. The center leaves are 10 cm. in length and 10½ cm. wide. The leaflet serrations are abundant, medium deep and acute. The serration at the apex of the leaf is a trifle smaller than the others. The apex of the serrations is often cupped downward. The central leaf is round in shape. There is a gradual cupping upward of the leaf from the main vein to the serrations. The surface of the leaf is mildly rugose. Dark green is the color of the leaves. The lower surfaces of the leaves are a light silver gray green.

The petioles, petiolules and the veins and under sides of the leaves are abundantly pubescent. There is also a small amount of very fine pubescent growth on the upper surface of the leaves.

RUNNERS

The runners are light green to red in color. They are vigorous and produce a large number of new plants. These can be used for propagation or they may be pruned. The remaining plants will then produce more fruit.

INFLORESCENCE

Inflorescence is usually from 16 to 28 cm. long. Also, the common peduncle is 11 to 14 cm. in length. Secondary peduncles may be two or three in number. Pedicels holding primary berries originate at the axil formed by the union of peduncles. Primary berries also develop from the pedicel originating from the axil of the secondary peduncle. The berries may all be on the pedicels originating from the axil of the common peduncle only. Secondary berries are smaller than primaries. All the bracts, including those of the common peduncle axil and those of the axils of the secondary peduncles are green. The pedicels near the calyx vary in color from green to reddish. There is an abundance of flowers which have petals that vary in number from 5 to 9 per blossom. The flowers measure up to 35 mm. in diameter. The blossoms have numerous stamens, they are also self pollinated.

The common peduncles, secondary peduncles and pedicels are abundantly pubescent.

FRUIT

The size of the berries is medium to large from June through the summer months and extending into September and October until frost. Primary berries have measured from 40 mm. in length and 40 mm. in width up to 60 mm. in width and 40 mm. in length. The shape of the berries varies, some are wedge, while others are conical. Shoulders are round and not necked. Flesh and epidermis are firm and the seeds are slightly exserted. Seeds are medium in size and vary in color from yellow to orange and red. The fruit is red near the epidermis, gradually becoming pink at the core. The larger berries have a characteristic cavity at the core. The fruit has a high dessert quality and keeps well under refrigeration and is excellent for freezing. The berries also have a ridged character to the outer surface which tends to strengthen the structure of the fruit. Medium red is the color of the berries, similar to Ozark Beauty. They also have a high gloss.

CALYX

The diameter of the calyx is 25 mm. to 38 mm. The upper and lower surfaces of the sepals are dark green. The sepals are ovate with acute tips. The calyx is usually held near the fruit surface.

I claim:

1. The new and distinct variety of strawberry plant herein described and identified by the characteristics enumerated above.

No references cited.

ROBERT E. BAGWILL, Primary Examiner